(12) United States Patent
Tomka et al.

(10) Patent No.: US 6,790,495 B1
(45) Date of Patent: Sep. 14, 2004

(54) METHOD FOR MANUFACTURING A SHAPE BODY CONTAINING A STARCH, A HOMOGENISED MASS CONTAINING STARCH AND A DEVICE FOR MANUFACTURING A SOFT CAPSULE

(75) Inventors: Ivan Tomka, Zürich (CH); Dieter Engel, Zuzwil (CH); Erich Brocker, Kirchberg (CH); Rico Ménard, Zürich (CH)

(73) Assignee: Peter Greither, Kirchberg (CH)

( * ) Notice: Subject to any disclaimer, the term of this patent is extended or adjusted under 35 U.S.C. 154(b) by 0 days.

(21) Appl. No.: 09/606,219

(22) Filed: Jun. 29, 2000

(30) Foreign Application Priority Data

Nov. 19, 1999 (EP) .......................................... 99811071.2

(51) Int. Cl.[7] .......................... B29D 22/00; B29D 23/00; C08L 3/00
(52) U.S. Cl. ...................... 428/35.2; 524/47; 424/451; 424/452; 424/455; 424/456; 514/962
(58) Field of Search .................. 424/455, 456, 424/451, 452; 514/962; 423/35.2; 524/47

(56) References Cited

U.S. PATENT DOCUMENTS

| | | | | |
|---|---|---|---|---|
| 4,673,438 A | * | 6/1987 | Wittwer et al. ............ | 106/126 |
| 5,098,606 A | * | 3/1992 | Nakajima et al. ........... | 252/358 |
| 5,462,980 A | * | 10/1995 | Bastioli et al. .............. | 524/47 |
| 5,569,692 A | * | 10/1996 | Bastioli et al. .............. | 524/47 |

FOREIGN PATENT DOCUMENTS

| | | |
|---|---|---|
| WO | 90/05161 | 5/1990 |
| WO | 90/14938 | 12/1990 |
| WO | 92/09274 | 6/1992 |

\* cited by examiner

*Primary Examiner*—Harold Pyon
*Assistant Examiner*—Patricia L. Nordmeyer
(74) *Attorney, Agent, or Firm*—Nath & Associates PLLC; Gary M. Nath; Jerald L. Meyer (57) ABSTRACT

The invention relates to a method for manufacturing a starch-containing shape body and a homogenised, starch-containing mass and shape bodies manufactured therefrom. The method is carried out in a manner such that the value of the limiting viscosity index of the mass manufactured therewith is at least 40 ml/g. Such a valve of the limiting viscosity index ensures an elongation at rupture of the extruded material of at least 150%, by which means soft capsules with a one-part capsule casing may be manufactured with the rotary die process.

20 Claims, 3 Drawing Sheets

METHOD FOR MANUFACTURING A SHAPE BODY CONTAINING A STARCH, A HOMOGENISED MASS CONTAINING STARCH AND A DEVICE FOR MANUFACTURING A SOFT CAPSULE

The invention relates to a method for manufacturing a shape body containing a starch, a homogenised mass containing starch and a device for manufacturing a soft capsule according to the preambles of the independent claims.

Form bodies from biodegradable materials for reasons of environmental protection have been of extraordinary interest for a long time. As a result of the problems with BSE in particular capsules with a capsule casing of gelatine-free materials have been gaining importance for the administration of pharmaceutically effective substances.

In a series of publications the manufacture of insert capsules from starch are described, such as in EP 118 240 and U.S. Pat. No. 4,738,724. In insert capsules are premanufactured as a two-part casing with the injection moulding method, where appropriate after intermediate storage filled with highly viscous or solid active substances. On account on unsealedness of the insert connection insert capsules are not suitable for low viscous fluids. Furthermore the manufacturing process of a filled insert capsule is complicated and expensive since the working steps of manufacture and filling the capsule casing must be carried out separate from one another.

For pumpable, in the broadest sense fluid capsule content materials, capsules with a one-part capsule casing of gelatine have proven themselves and these may be manufactured in continuous automatisable methods. The manufacture of the capsule casing and the filling of this at the same time is effected in a single working step. In this continuous, 1-step method shape parts are manufactured from which the capsule casing during and after the filling are joined together by welding the outer edges of the shape parts. The shape part manufacture is effected either by way of diverging and converging forms, such as with the Norton, Banner or Schering process or by way of rotating shaping drums, as is e.g. realised in the rotary die process and in the Accogel method ("Die Kapsel" Fahrig/Hofer—Publisher, Stuttgart 1983; Lachmann/Liebermann/Kanig, "The Theory and Practice of Industrial Pharmacy"; Third Edition, Philadelphia 1986). The filling is effected with the help of metering pumps which deliver a defined quantity of active substance during the punching out and welding of the shape parts for forming a one-piece capsule casing. The welding, i.e. the forming of the seams is effected generally by way of pressure and heat. The manufacturing costs are considerably reduced with respect to two-part insert capsules.

U.S. Pat. No. 5,342,626 describes the manufacture of capsules in the rotary die process, wherein the capsule casing material consists of carrageen, mannan gums, such as e.g. galactomannans and glucomannans, gelan or mixtures amongst one another. These macromolecular vegetable biopolymers are however not acceptable with respect to cost since the raw materials are too expensive.

The manufacturing process for one-part capsules sets a series of demands on the capsule casing material. One of the main preconditions is the capability of the capsule casing material to form highly elastic "endless" tapes with a sufficient strength. The capsule casing must when required dissolve rapidly in the stomach and intestinal tract in order to be able to release the active substances. The capsule casing material must be weldable. The molecules of the material forming the shape parts, in particular the macromolecules of the polymer should at the location of the seam ideally penetrate in order to ensure a sufficient stability of the seam location. Gelatine fullfills all these conditions in an almost ideal manner and until now could not be replaced as a material for one-part gelatine capsules.

Under the criteria of availability and cost starch for the manufacture on one-part capsule casings is also a desirable initial material.

The manufacture of starch films has already been described several times, the combination of properties which such a starch film must have for manufacturing one-part capsules has not been achieved up to now.

EP 474 705 describes a method for manufacturing starch shape bodies by extrusion of a starch molten mass. The starch molten mass contains starch with an amylose content over 50% and aggregates. From the molten mass, before, during and/or after the extruding the water is removed by applying a vacuum. The foils extruded from this material have an elongation at rupture between 80 and 200%. Starches with a high amylose content are not suitable as capsule casing materials since the tendency of the amylose chains to retrograde stands in the way of a quick dissolving of the capsule casing.

EP 0397 819 discloses a method for manufacturing thermoplastically processable starch, wherein the crystalline part in the starch lies below 5%. The method consists of mixing native starch with at least 10% by weight of an aggregate which has a solubility parameter of at least 30.7 $(MPa)^{1/2}$. The mixture with the supply of heat is conveyed into a molten mass at a temperature between 120° C. and 220° C. The water content of the starch already in the molten mass is reduced to below 5%. The molar mass of the applied starch before conveying into the thermoplastic condition is larger than 1,000,000 Daltons, preferably between 3,000,000 Daltons and 10,000,000 Daltons. Although this method yields a thermoplastic starch with a good workability into shape bodies which have a sufficient strength, the elongation at rupture of the shape bodies manufactured with this thermoplastic starch only reaches values between 40 and 55%. The elasticity of the starch film is thus to low for the manufacture of one-part capsule casings in a continuous method and leads to a tearing of the shape parts on manufacture or to a tearing of the finished capsule.

The starch film which is produced according to the method disclosed in EP 397 819 furthermore also does not show the weldability or strength of seam which would be sufficient for the demands with respect to the quality on one-part capsule casings.

EP 304 401 likewise describes a method for manufacturing shaped objects from starch. The thermoplastic starch molten mass required for this is manufactured from a pre-treated starch. The destructurisation (destruction of the crystalline region) of the native starch and the subsequent homogenisation (conveying into the thermoplastic condition) in each case takes place at temperatures between 120° C. and 190° C. in a closed vessel with a water content between 10 and 20%. The elongation at rupture of starch films manufactured according to this method is not sufficient for the production of one-part capsule casings in a continuous method. The starch films show furthermore also an insufficient weldability and seam strength.

EP 0 542 155 discloses biodegradable shaping masses which amongst other things are suitable for the manufacture of film.

The shaping masses apart from thermoplastically processable starches contain cellulose derivatives. The elongation at rupture exceeds the value of 85% but not that which is sufficient for the manufacture of one-part capsule casings in a continuous method. The weldability of the films is unsatisfactory. Many of the polymer blends disclosed in EP 542 155 contain substances which are not allowed for pharmaceutical application or for foodstuffs.

WO 97/35537 discloses one-part capsules manufactured by way of rotating shaping drums and containing jellied starch. The teaching of the part etching of the film surface disclosed here has shown to be disadvantageous for the manufacture of one-part capsules with respect to the transport and pressure stability (on pressing the capsules out of the blister packages) since the capsule casings at the region of the seam location by way of this become too soft and flexible.

The object of the present invention is to avoid the problems of the state of the art.

In particular the object of the present invention lies in making available a method for the manufacture of gelatine-free shape bodies.

A further object lies in preparing a mixture containing a starch which by way of semi-continous or continuous method, in particular by way of the rotary die method may be processed to one-part capsule casings.

A further object lies in preparing one-part soft capsules based on starch, wherein the starch films for manufacturing the capsule casing is to have an extension at rupture of at least 100%.

A further object lies in preparing starch films with a good weldability.

A further object lies in manufacturing starch capsules with a one-part capsule casing in a continuous method which after a storage duration of one year neither exhibits unsealedness, in particular at the seam location, nor changes in the dissolving speed of the capsule casing.

These objects are achieved by the features of the independent claims.

In particular they are achieved by a method for manufacturing a shape body containing a starch, in particular a soft capsule with a one-part capsule casing, wherein the method comprises the following steps a) conveying a mixture containing at least one starch, water, and at least one organic softener, whilst melting and kneading, into a homogenised thermoplastic molten mass in a first processing means;

b) where appropriate manufacturing an intermediate product capable of storage, in particular a granulate after cooling of the homogenised molten mass and subsequent melting of the intermediate product in a second processing means;

c) manufacturing at least one material line, in particular an extruded film, at the exit of the first or where appropriate second processing means, d) re-forming the material line into a shape body in a continuous or intermittent shaping method;

e) where appropriate drying the shape body, wherein the steps a) to c) are carried out in a manner such that in step d) there results a value of the limiting viscosity index $[\eta]$ of the mass forming the material line of at least 40 ml/g, preferably of at least 50 ml/g and even more preferred of at least 60 ml/g.

The mixture applied in step a) contains a starch preferably in a weight range of 45 to 80% by weight with respect to the total weight of the mixture.

The term "one-part" is to be understood as a differentiation with respect to two-part capsules which are produced by way of inserting and/or adhesing the two capsule parts with outer edges lying over one another. The one-part capsule casing may completely be without a seam location or when it is formed from shape parts may be formed with a welded seam location.

In a preferred embodiment form the mixture applied in step a) additionally contains an inert lubricant and releasing agent which is selected from the groups consisting of lecithins, monoglycerides, diglycerides or triglycerides of nutrient fatty acids, polyglycerine ester of nutrient fatty acids, polyethyleneglycol ester of nutrient fatty acids, sugar ester of nutrient fatty acids and nutrient fatty acids.

The lubricant and releasing agent is contained in the mixture preferably in a range of 0 to 4% by weight with respect to the total weight of the mixture. Preferably it is added in the mixture at 0.5 to 2% by weight and even more preferred in 0.8 to 1.5% by weight.

In a preferred embodiment form the mixture applied in step a) contains glycerine monostearate and lecithin in a weight ratio of 1:1.5, preferably of 1:1.2 and even more preferred of 1:1.0. Glycerine monostearate and lecithin in this weight ratio act very advantageously on the weldability as well as on the weld seam strength.

Nutrient fatty acids are to be understood as acid components of the triglycerides of monocarbon acids occurring in natural fats. They have an even number of C atoms and have an linear carbon network. The chain length of the fatty acids varies from 2 to 26 atoms. A large group of the fatty acids are saturated fatty acids.

The term soft capsule is to be understood as a product of the common continuous and semi-continuous, 1-step manufacturing method for one-part capsules cited in the literature. The term at the same time does not serve so much as a differentiation of the softener content since also hard capsules, as a description for joined together two-part capsules, may contain a softener content of up to 12% with respect to the total mass.

The term starch is to be understood as native starches as well as physically and/or chemically modified starches. For the mixture used in step a) of the method according to the invention all starches independent of the plant from which it is extracted are suitable. In a preferred embodiment form it is the case of starch whose amylo pectine content lies above 50% with respect to the total weight of the water-free starch. Potato starch has shown to be particularly suitable for the method (described here).

In a further preferred embodiment form it is the case of the starch of a pasted starch. Above a temperature typical for each type of starch in aqueous starch suspensions after reaching the highest degree of swelling a "solution" occurs, i.e. irreversible disintegration of the molecules. This procedure is called "gelatinisation". The gelatinisation, i.e. the irreversible swelling at a high temperature of up to 40 times the original volume involves a gradual uptake of water and dissolving of hydrogen bridge bonds which permits a further hydration up to the complete disintegration of the starch granule joint.

The conveying of the mixture containing the starch into the thermoplastic, homogenised condition in step a) just as the subsequently following processing steps b) and c) must be effected under conditions which prevent an uncontrolled breakdown of the amylose and amylo pectin mass to short fragments.

The processing parameters such as e.g. temperature, pressure, sojourn time and kneading power during the steps a) to c) must be matched to one another such that the limiting viscosity index $[\eta]$ of the homogenised mass forming the material line in step d) is at least 40 ml/g. In a preferred embodiment form the limiting viscosity index [η] is at least 50 ml/g and even more preferred at least 60 ml/g.

By way of the steps a) to c) a mass must be produced in which there are essentially no longer present any crystalline regions in the starch. Crystalline regions in the extruded material line lead to the formation of pinholes, i.e. to inhomogenities in the material which then have a particularly disadvantageous effect when the material line in step c) is an extruded film. "Essentially no longer present any crystalline regions" is thus to be understood as a material or mass which at every location in the material has essentially the same chemical and physical composition and nature. Slight deviations may occur on the respective material or shape part surface by way of the uptake of air humidity.

The limiting viscosity index [η] or also border viscosity within a polymeric homologous row has the following relation to the molar mass and the weight average of the molecular weight distribution $$[\eta]=K \times M^\alpha$$

wherein $\alpha$ is an exponent dependent on the molecule shape and the K-value a constant dependent on the dissolved substance and on the solvent. The limiting viscosity index within a polymeric homologous row is larger the larger is the molecular weight of the polymer with otherwise unchanged parameters. The measurement of the limiting viscosity index is not able to do an evaluation of the absolute molecular weights.

Without delivering an exhaustive explanation it is assumed that first of all the polymerisation degree of the branched amyl pectin molecules of the applied starch is shown to be responsible for the elasticity of the material line produced in step d). The polymerisation degree and the molecular weight of the amyl pectin should be sufficiently high. This is particularly of great importance for a web-like film which is formed in the 1-step method to a soft capsule.

Additionally to the inherent elasticity of the amyl pectin molecules, with a sufficient polymerisation degree also a type of "starch network" may be constructed by way of interlacing and interlocking by way of the branches of the amyl pectin molecules. But also amylose molecules, with a sufficiently high polymerisation degree, may participate in this "starch network".

The re-forming procedure of the material line into a shape body, in particular the re-forming of an extruded film into a one-part soft capsule with the method known in the technology demands extensions at rupture of the material line, in particular of the film, of at least 100% at 25° C. and 60% relative air humidity. In a preferred embodiment form the extension at rupture of the material line, in particular the film is at least 160% and even more preferred at least 240%.

Extensions at rupture of 100t may with the starch-containing mass manufactured according to the method according to the invention may be achieved when the limiting viscosity index of the mass is at least 40 ml/g, preferably at least 50 ml/g and even more preferred at least 60 ml/g.

Apart from the extension at rupture the maximum strength $\sigma_m$ of the line plays an important role for the properties of the shape body manufactured therefrom. The strength is of a particular importance when with the material line it is the case of a film with which in the re-forming process a one-part capsule casing is formed. The strength $\sigma_m$ of the material line produced in step c), in particular the film, at 25° C. and 60% relative air humidity must be at least 2 MPa. In a preferred embodiment form it must be in a region of 3.5 MPa to 8 MPa and even more preferred in a region of 4 MPa to 6.5 MPa.

The strength is also related to the limiting viscosity index [η]. It has been found that $\sigma_m$ of the material line resulting in step c) is larger the larger is the limiting viscosity index of the mass forming the material line.

The chemical substitution of the starch hydroxyl groups under formations of ether, esther, vinyl and acetal may be advantageous since they encourage the formation of the "starch networks". Advantageously are in particular hydroxypropyl starch derivatives. A hydroxypropyl starch derivative with a DS=0.1 (DS=Degree of Substitution) apart from very good film forming properties also shows a good fulfilment of the above mentioned parameters.

Since step d) and step e) are effected under conditions which does not effect a further breakdown of the amylose pectin and amylo pectin molecules, the molecules with respect to the polymerisation degree (and thus limiting viscosity of the mass forming the shape parts) also in the resulting shape body and in particular in the capsule casing are present unchanged.

The effect of the various processing parameters on the breakdown of the starch molecules and thus on the development of the limiting viscosity index are known to the man skilled in the art. Thus e.g. also at relatively high temperatures a substantial breakdown of the starch molecules may be avoided when the sojourn times of the mass containing the starch at these temperatures are kept small.

In a preferred embodiment form the temperature of the molten mass in the first and where appropriate second processing means, as well as on manufacture of the material line does not exceed 160° C., preferably 120° C. and even more preferred 90° C. At 160° C. in particular also the disintegration procedure in step a) would be completed in less than 5 minutes, preferably less than 3 minutes.

In a further preferred embodiment form the energy used by the kneading on producing the homogenised thermoplastic molten mass in step a) to c) does not exceed 0.3 kWh/kg, preferably 0.2 kWh/kg and even more preferred 0.175 kWh/kg.

The softener content of the mixture used in step a) is at least 12% by weight with respect to the weight of the water-free starch. In a preferred embodiment form the content of the softener is in a region of 30% by weight up to 50% by weight and even more preferred in a region of 38% by weight to 45% by weight.

By way of the extensive exclusion of heavily broken down oligomers of the starch effected by the course of the process it is possible to work into the homogenised mass the high quantities of softeners as are provided for in the preferred embodiment examples. Oligomers such as e.g. maltodextrine in the thermoplastic molten mass or in the product resulting therefrom would likewise display a softening effect and the working in of additionally large quantities of preferred "external softener" would no longer be possible.

Preferably those softeners are applied which have a solubility parameter equal to or >16.3 $(MPa)^{1/2}$. The softeners are selected from the group consisting of polyalcohols, organic acids, amines, acid amides and sulphoxides. Preferably they are polyalcohols. Glycerin has shown to be a suitable softener.

It has been surprisingly ascertained that the content of glycerine in the mixture applied in step a) in certain weight ranges may be replaced by water without there leading to a worsening of the properties of the shape body produced in step d). In particular the elongation at rupture with a replacement of the glycerine by water in the ratio 2:1 (2 parts glycerine are replaced by 1 part of water) is not reduced. The glycerine content is however at least 12% by weight with respect to the weight of the water-free starch.

To the mixture applied in step a) according to the required properties of the shape body resulting in d) and e) there may yet be added at least one aggregate in a weight range of 3.5% by weight to 15% by weight, preferably from 5% by weight to 8% by weight with respect to the total weight of the mixture. The aggregates are selected from the group consisting of carbonates and/or hydrogen carbonates of alkali ions or alkaline earth ions, further decomposing agents, colourings, preservatives, antioxidants, physically and/or chemically modified biopolymers, in particular polysaccharides and vegetable polypeptides.

The opacity of the homogenised mass is e.g. achieved preferably with the addition of titanium dioxide as a filler.

As a decomposing agent, for a quick decomposition of the capsule casing preferably calcium carbonate and amylases are added.

The group of the physically and/or chemically modified biopolymers comprises cellulose, in particular part hydroxypropylised cellulose, alginate, carageenan, galactomannans, glucomannans, casein.

The homogenised starch molten mass may in step c) be extruded directly by way of a wide-slot nozzle into a starch film or starch tape. The molten mass may however also be cooled, dried and processed into a granulate capable of storage (with the sealing from dampness). This granulate may be stored and is available for a later processing. Optionally to the molten mass processed to a granulate there may also only be added a part of the necessary lubricant and releasing agent, softener and aggregates. For example the addition of animal and/or vegetable fat for preventing undesired colour effects may be done away with and this admixed only when the granulate is again remelted in the second processing means.

The extruded tapes are now either directly processed further or where appropriate wound up for storage on drums using plastic foils as an intermediate layer. With this, polyethylene has shown to be a suitable foil material.

The starch film according to the invention may in particular by processed for the manufacture of soft capsules on all installations known in the technology for manufacturing one-part capsules. Particularly suitable have shown to be continuous installations and in particularly the rotary die process. The capsule wall with this, under the effect of heat, is welded from two shape part halves which have been previously punched out of the starch film. Two "endless starch films" are led through two neighbouring rollers or drums having reliefs, these rollers or drums rotating in opposing directions. Whilst the starch film is pressed into the relief and thus the capsule halves are formed, the pumpable or injectable capsule filling is exactly metered by way of a valve and via a filling wedge is introduced into the entry let-in of the shaping drums. The shape and size of the capsule is thus dependent on the geometric dimensions of the reliefs in the drums and the metered filling volume.

To be consistent the term capsule is thus not only to be understood as the typical capsule shape, but also every other form of "casing" such as e.g. balls, cushions and figures. Until today there exist numerous further developments and deviations from this basic principle.

The one-part capsule casings manufactured by way of the starch film according to the invention may be additionally coated, e.g. in order to delay the release of active substances.

The coextrusion, coating and laminating of the starch film according to the invention with materials whose film-forming property is based on synthetic and/or natural polymers creates additional possibilities of forming certain properties of the capsule casing by way of a multi-layer foil.

In particular by way of the multi-layer construction a starch foil may be manufactured which on the inner side has an easily weldable coating whilst the outer side is coated in a manner such that a delayed effect of the breakdown of the capsule sets in.

The water constituent part of the mixture applied in step a) may in the method according to the invention be changed in a directed manner in step b) or c).

Part of the present invention is therefore further a homogenised starch containing mass which contains an essentially amorphous starch preferably in a weight range of 45 to 80 with respect to the total weight of the mass with an amyl pectin content greater than or equal to 50% by weight with respect to the weight of the water-free starch, furthermore water, at least one organic softener in a constituent part of at least 12% by weight with respect to the weight of the water-free starch, wherein the limiting viscosity index of the homogenised mass is at least 40 ml/g.

Preferably the limiting viscosity index is at least 50 ml/g, even more preferred at least 60 ml/g.

In a preferred embodiment form the content of organic softeners lies in the range of 30% by weight to 50% by weight, preferably in a range of 38% by weight to 45% by weight.

In a further embodiment form the mass additionally contains a lubricant and releasing agent, which is selected from the group consisting of lecithins, monoglycerides, diglycerides and triglycerides of edible fatty acids, sugar ester of edible fatty acids and edible fatty acids.

The softener is preferably selected from the group consisting of polyalcohols, organic acids, hydroxy acids, amines, acid amines and sulphoxides. In a preferred embodiment form glycerine is applied as a softener.

In a further embodiment form the mass additionally may contain yet at least one aggregate in a weight range of 3.5% by weight to 15% by weight with respect to the total weight of the mass, preferably from 5% by weight to 8% by weight. The aggregate is directed towards the required properties of the shape body produced from the homogenised mass and is selected from the group consisting of carbonates and/or hydrogen carbonates of alkali and/or alkaline earth ions, further decomposition agents, colourings, preservatives, antioxidants, physically and/or chemically modified biopolymers, in particular polysaccharides and vegetable polypeptides. Preferably as a decomposition agent for the one-part capsule casing calcium carbonate and amylases are applied.

The shape body, in particular the capsule casing has an elongation at rupture of at least 100%, preferably at least 160% and even more preferred at least 240%.

The shape body, in particular the soft capsule casing at 25° C. and 60% relative air humidity has a strength $\sigma_m$ of at least 2 MPa, preferably a strength in the range of 3.5 MPa to 8 Mpa and even more preferred from 4 MPa to 6.5 MPa.

Part of the invention furthermore are shape bodies which are manufactured from the mass according to the invention. Preferably the shape body is a one-part capsule casing.

The shape body, in particular the capsule casing has a thickness in the range between 0.1 and 2 mm, preferably between 0.2 and 0.6 mm.

In a further preferred embodiment form the shape body, in particular the soft capsule casing consists of a multi-layer film. At least two of the films have a different chemical composition.

Disregarding the manufacture of one-layered capsule casings the thermoplastically processable starch molten mass may also be used for the manufacture of any other type of shape body, in particular packaging materials.

In a preferred embodiment form the shape body has a water content of maximal 15% by weight, preferably 7% by weight and even more preferred 5% by weight with respect to the total weight of the mass.

For guiding the film or tape there are required no lubricants at all. Also the welding of the capsule halves is effected without the addition of any solvents on the film surface which would serve an initial adhesing of the joined-together shape parts.

One embodiment example of the invention in an aspect with regard to the device is represented in the figures and is hereinafter explained in more detail. There are shown in FIG. 1 the elongation at rupture $[\epsilon_b]$ of the mass according to the invention containing starch, in dependence on the limiting viscosity index $[\eta]$, FIG. 2 the maximum strength $[\sigma_m]$ of the mass according to the invention containing starch, in dependence on the limiting viscosity index $[\eta]$, FIG. 3 a heavily schematised representation of a filling and shaping station in the rotary die method and FIG. 4 the symbolic representation of a double screw-type extruder with the temperature conditions prevailing therein.

The manufacture of the samples which in FIG. 1 demonstrates the connection between the elongation at rupture and the limiting viscosity index, is effected in the following manner starch: 56.2 to 56.9% by weight glycerine: 41.8% by weight with respect to the content of the water-free starch water 1.3–2.0% by weight with respect to the total weight of the mixture.

The measurement of the elongation at rupture is effected according to DIN Standard 53455 and DIN EN ISO 527-1 to ISO 527-3. The mixtures were homogenised in a Brabender kneader at 160 rpm with a kneading time of in each case 15 min and at kneading temperatures of 110° C., 160° C., 200° C., 220° C. and 235° C. With an increasing temperature as a result of the thermal decomposition there was ascertained a clear brown colouring.

The measurement of the limiting viscosity index $[\square]$ is effected analogously to the DIN Standard: DIN 51562-1 to 51562-4. However the glycerine content of the samples and its influence on the run-through times in the Ubbelohde vicosity meter now had to be taken into account. For this firstly the influence of the glycerine content on the run-through time to was determined, by way of the obtained calibration lines then the run-through times $t_{0Gly}$ could be calculated with any glycerine content according to $$t_{0Gly}=t_0 \cdot (1.00002+0.00238 \cdot C_{Gly})$$

wherein $C_{Gly}$ is the concentration of glycerine present, in mg/ml. The limiting viscosity index determined for the broken down starches together with the mechanical properties of the associated samples are set up in Table 1.

Figure 1:
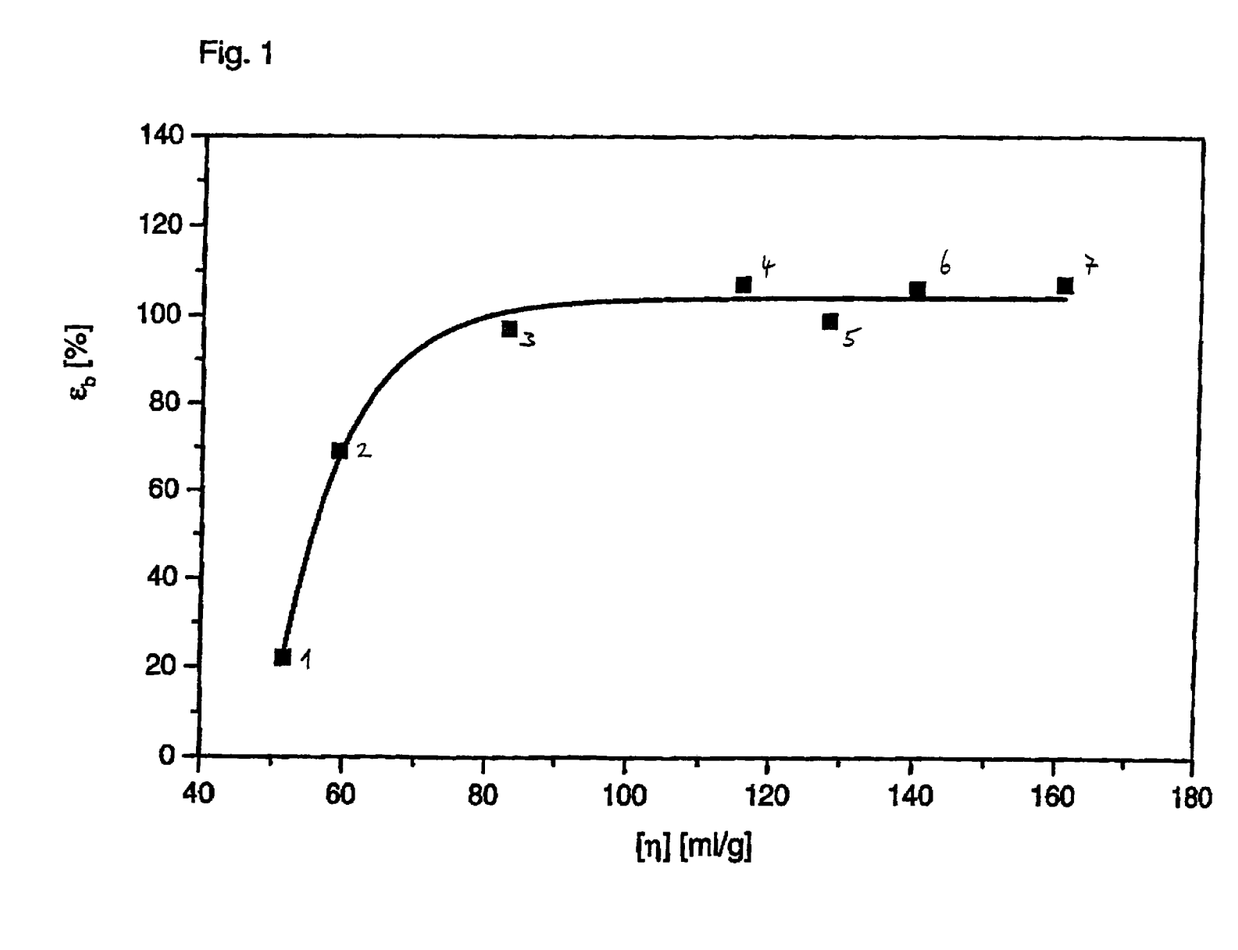

The dependence shown in FIG. 1 of the elongation at rupture of the mass according to the invention containing starch on the limiting viscosity index of the mass shows a rise of the elongation at rupture at a value of the limiting viscosity index of 51.5 ml/g. The elongation at rupture rises to a value of 97%.

97% elongation at rupture is reached at a limiting viscosity index of 82.8 ml/g. Thereafter the elongation at rupture runs with an increasing value of the limiting viscosity index asymptotically to a limit value of approx. 105%.

With a low constituent part of the softener constituent part the curve as a whole runs flatter, i.e. shifted to deeper elongations at rupture. The initial value of the limiting viscosity index, i.e. the value from which a noticeable rise of the elongation at rupture is observed is dependent on the softener constituent part and singly dependent on the molecular weight means of the starch molecules or the corresponding limiting viscosity index. Table 1 draws up the values graphically shown in FIGS. 1 and 2.

The maximum strength $\sigma_m$ was determined analogously to DIN Standard 53455 and DIN EN ISO 527-1 to ISO 527-3. For the dependence shown in FIG. 2 the same sample material was used which was measured for the elongation at rupture in FIG. 1.

Figure 2:
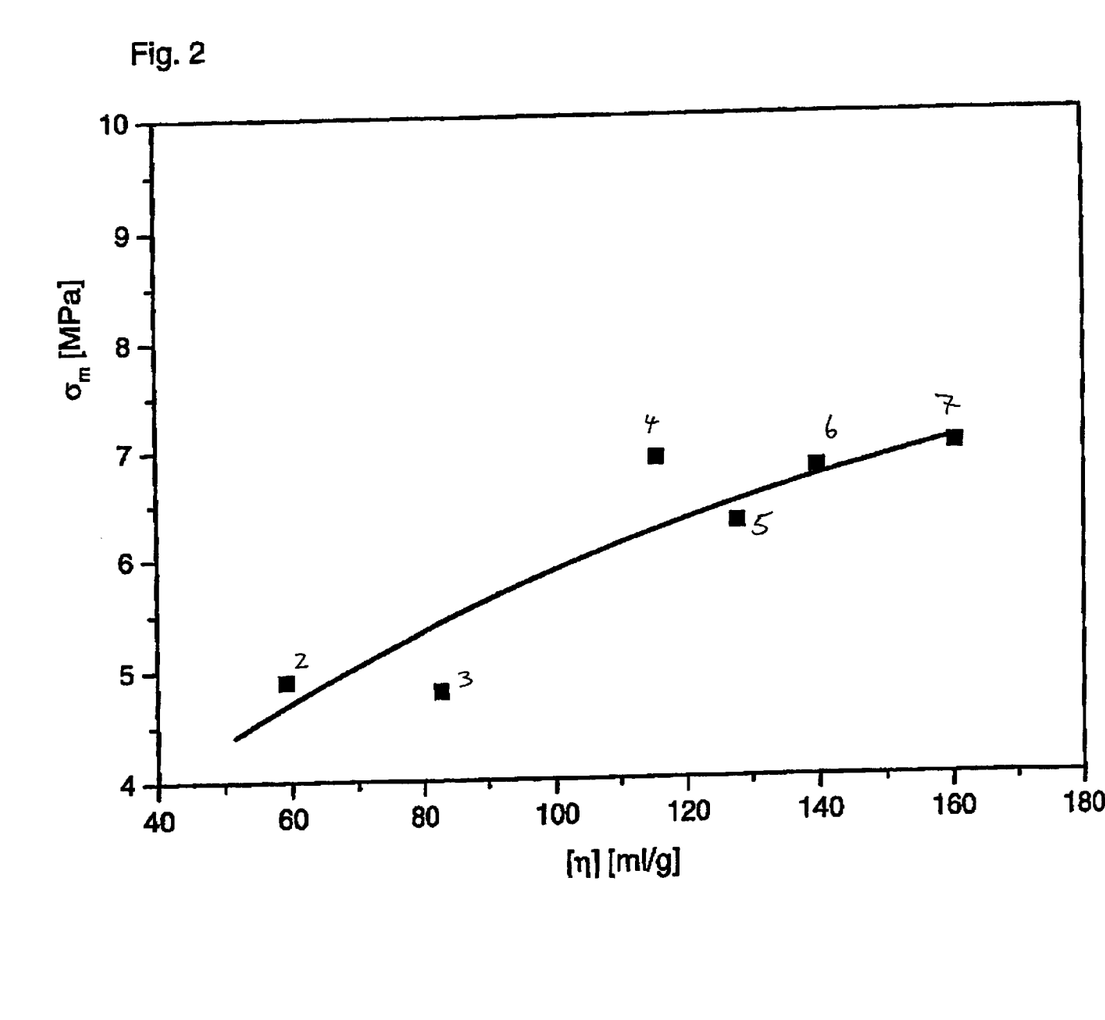

The relation between the maximum strength am and the limiting viscosity index $[\eta]$ is evident from FIG. 2, where a reduction in the strength may be ascertained with a reducing limiting viscosity index.

Figure 3:
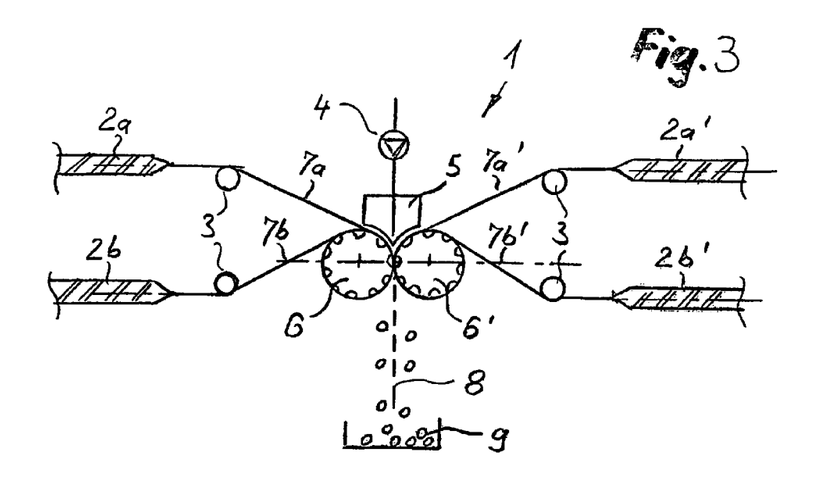

The filling and shaping station indicated as a whole at 1 in FIG. 3 comprises for the encapsulation a shaping drum pair 6, 6', wherein in the surface of the shaping drums there are arranged the recesses necessary for shaping the capsules. In the entry let-in of the shaping drum pair there is arranged a filling wedge 5 through which by way of a delivery pump 5 the filling material may be introduced. With the present embodiment example the capsule casing consists of two layers with different material properties which are formed by the two starch films 7a, 7a' on the one hand and 7b, 7b' on the other hand. These two starch films are prepared in the worm-type extruders 2a, 2a' and 2b, 2b' and via diverting drums 3 directly and with the same conveying speed are led to the entry let-in of the shaping drum pair 6, 6'. The worm-type extruders are with this arranged next to the filling and shaping station and where appropriate arranged on the same machine frame.

The starch films are between the shaping drum pair shaped and welded into a one-part soft capsule, wherein they enclose the filling material. The individual capsules 9 are collected and in any case led to a drying process whilst the remaining film skeleton 8 possibly by recycling is again processed to new capsules.

Figure 4:
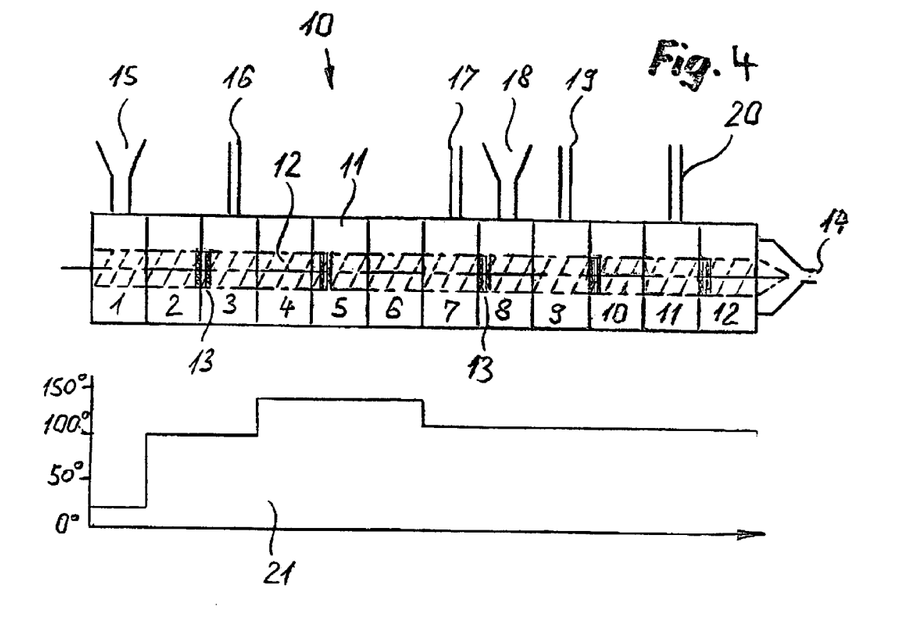

FIG. 4 shows in a heavily simplified manner a double worm-type extruder 10 which in the present case is composed of twelve individual housing blocks 1–12. The housing blocks are continuously numbered from left to right. Each housing block may be electrically heated with a separate control circuit and/or be cooled with valve-controlled influxes with cold water. Furthermore individual blocks may be provided with connection pieces as will yet be explained hereinafter. In the present case it is the case of equally rotating, tightly meshing double worm-type extruders, wherein the diameter of a worm is 44 mm. The length of the whole worm shaft is 2,112 mm, which corresponds to a ratio of length to diameter of 48. At the end of the extruder the material is delivered via a nozzle 14. This nozzle may for example comprise twelve hole bores of 2 mm diameter. At the same time it would be conceivable for the manufacture of the granulate to hot-sprue the individual material lines and then lead them to a fluid bed dryer. At the nozzle 14 however also directly a finished material film may be removed.

On the worms 12 at suitable locations there are arranged kneading disks 13 of differing configurations in order to achieve as homogeneous as possible kneading of the material mixture. The block 1 is cooled with water and provided with a powder feed 15. The block 2 is closed whilst on block 3 there is arranged an injection nozzle 16 for a fluid metering into the kneading space. In the transition region of the blocks 2 and 3 there are arranged fine neutral kneading disks 13. The blocks 4 to 6 are again closed, wherein on block 5 there are provided broad, neutral and back-conveying kneading disks. Block 7 has at its disposal a connection conduit 17 which is connected to a vacuum source. On block 8 again there is arranged a powder feed 18 and the worm is provided with a fine, neutral or conveying kneading disk. Block 9 likewise has at its disposal an injection nozzle 19 whilst block 10 is closed. The worm in block 10 in contrast has at its disposal broad, neutral and back-conveying kneading disks. Block 11 has a further connection conduit 20 which may be connected to a vacuum source or to the atmosphere. Block 12 is closed, the worm here however has medium, conveying kneading disks.

Below the schematic conveying worm there is drawn up a temperature curve. The adjustable temperature accuracy is +/−30° C. With the specified temperatures it is the case of the block temperature which does not compellingly need to be identical with the temperature in the molten mass. The temperature in the molten mass is evidently still influenced by other parameters, in particular by the rotational speed of the worm. With the extrusion it is therefore necessary to take account of these conditions and to match the adjustable variables to one another such that optimal material properties are achieved.

With the embodiment example described by way of this Figure a rotational speed of 340 revolutions per minute (rpm) is made. The total throughput is approx. 34.3 kg/h and the energy uptake approx. 0.175 kWh/kg. To the block 1 held at 20° C. there is metered 20 kg/hour (approx. 60%) of starch powder. The powder is entered with shifting edges and then supplied to the blocks 2 and 3 heated to 100° C. With block 3 there is effected a metering of 11 kg/h (approx. 30%) glycerine with a working pressure of at least 10 bar via a gravimetric piston pump. In the closed blocks 4 to 6 the temperature is increased to 140° C. With block 7 there is applied a vacuum of 800 mbar, wherein approx. 6% water exits. The temperature is now again taken back to 110° C. With block 8 there is effected a supply of 1.4 kg/h (approx. 10%) of calcium carbonate. Where appropriate at block 9 1.9 kg/h (approx. 5 to 8%) of glycerine may be metered. The working pressure is likewise at least 10 bar. If this connection is not required it is closed with a blind plug. At block 11 again there is applied a vacuum, wherein approx. 2 to 4% water exits. Where appropriate an atmospheric aeration is also sufficient.

The temperature of the molten mass may at no location of the extruder exceed 160° C. since otherwise a thermal breakdown of the starch sets in. Furthermore it is the case that the thermal change of the starch is smaller, the shorter the molten mass is subjected to a higher temperature. Therefore an optimal relation between temperature control and material throughput must be created.

The present invention is further explained by way of the subsequent examples:

EXAMPLE 1

Via a two-shaft extruder (type ZSK 30, Werner & Pfleiderer) the following components were continuously metered and melted

| | |
|---|---|
| starch: | 7.7 kg/h |
| lecithin: | 0.147 kg/h |
| glycerine monostearate: | 0.147 kg/h |
| glycerine (99.5 purity): | 4.47 kg/h |
| calcium carbonate, precipitated: | 1.0 kg/h | wherein with a worm rotational speed of 180 rpm one extruded under the following conditions (see FIG. 2):

| | |
|---|---|
| block 1: | 25° C. |
| block 2 and 3 | 100° C. |
| block 4 to 6 | 140° C. |
| block 7 to 9: | 110° C. |
| block 10 to 12: | 110° C. |
| nozzle: | 110° C. |

With respect to the water-free starch this corresponds to a glycerine content of 38.77%. With respect to the water-free end product there resulted the following constituent parts:

| | |
|---|---|
| lecithin: | 1.11% |
| glycerine-monostearate | 1.11% |
| starch (water-free): | 55.15% |
| CaCO$_3$: | 7.76% |

Specific energy uptake on extrusion: 0.275 kWh/kg

EXAMPLE 2

Via a two-shaft extruder (type ZSK 30, Werner & Pfleiderer) the following components were continuously metered and melted

| | |
|---|---|
| starch: | 7.7 kg/h |
| lecithin: | 0.147 kg/h |
| glycerine monostearate: | 0.147 kg/h |
| glycerine (99.5 purity): | 4.67 kg/h |

Wherein with a worm rotational speed of 260 rpm one extruded under the same conditions as in Example 1.

In block 4 alternatively a vacuum may be applied in order to remove excess water (from the starch powder) (e.g. 800 mbar).

With respect to the water-free starch this corresponds to a glycerine content of 39.81%. With respect to the water-free end product there resulted the following constituent parts:

| | |
|---|---|
| lecithin: | 1.18% |
| glycerine monostearate | 1.18% |
| starch (water-free): | 58.81% |

Specific energy uptake on extrusion: 0.233 kWh/kg

EXAMPLE 3

Via a two-shaft extruder (type ZSK 30, Werner & Pfleiderer) the following components were continuously metered and melted

| | |
|---|---|
| starch: | 7.7 kg/h |
| lecithin: | 0.147 kg/h |
| glycerine monostearate: | 0.147 kg/h |
| glycerine (99.5 purity): | 4.47 kg/h |

Wherein with a worm rotational speed of 260 rpm one extruded under the same conditions as in Example 1.

In block 4 alternatively a vacuum may be applied in order to remove excess water (from the starch powder) (e.g. 800 mbar).

With respect to the water-free starch this corresponds to a glycerine content of 38.77w. With respect to the water-free end product there resulted the following constituent parts:

| | |
|---|---|
| lecithin: | 1.20% |
| glycerine-monostearate | 1.20% |
| starch (water-free): | 59.79% |

EXAMPLE 4

Via a two-shaft extruder (type ZSK 30, Werner & Pfleiderer) the following components were continuously metered and melted

| | |
|---|---|
| starch: | 7.7 kg/h |
| lecithin: | 0.147 kg/h |
| glycerine-monostearate: | 0.147 kg/h |
| glycerine (99.5 purity) | 4.47 kg/h |
| calcium carbonate, precipitated: | 1.0 kg/h |

Wherein with a worm rotational speed of 260 rpm one extruded under the same conditions as in Example 1.

In block 4 alternatively a vacuum may be applied in order to remove excess water (from the starch powder) (e.g. 800 mbar).

With respect to the water-free starch this corresponds to a glycerine content of 39.81%. With respect to the water-free end product there resulted the following constituent parts:

| | |
|---|---|
| lecithin: | 1.09% |
| glycerine monostearate | 1.09% |
| starch (water-free): | 54.31% |
| $CaCO_3$: | 7.64% |

Specific energy uptake on extrusion: 0.254 kWh/kg

EXAMPLE 5

Via a two-shaft extruder (type ZSK 30, Werner & Pfleiderer) the following components were continuously metered and melted

| | |
|---|---|
| starch: | 7.7 kg/h |
| lecithin: | 0.147 kg/h |
| glycerine monostearate: | 0.147 kg/h |
| glycerine (99.5 purity): | 4.87 kg h |
| calcium carbonate, precipitated: | 1.0 kg/h |

Wherein with a worm rotational speed of 260 rpm one extruded under the same conditions as in Example 1.

In block 4 alternatively a vacuum may be applied in order to remove excess water (from the starch powder) (e.g. 800 mbar).

With respect to the water-free starch this corresponds to a glycerine content of 40.81%. With respect to the water-free end product there resulted the following constituent parts:

| | |
|---|---|
| lecithin: | 1.08% |
| glycerine monostearate | 1.08% |
| starch (water-free): | 53.49% |
| $CaCO_3$: | 7.53% |

Specific energy uptake on extrusion: 0.242 kWh/kg

The thus arising mass then formed through the nozzle to a line, this is then cooled at the surrounding air and finally granulated.

The thus obtained granulate in a one-worm extruder (chill-roll installation compression worm (1:3) of Göttfert) at 130° C. and 70 rpm is melted and led through a slot nozzle to a pair of water-cooled drums at a temperature of <40° C., and from here by way of a controllable winding installation (likewise from Göttfert) is wound up with an intermediate layer of polyethylene foil.

Two such identical foil windings in the next working step are continuously unwound and after releasing the polyethylene intermediate layer is led to the two embossing drums of a rotary die installation.

TABLE 1

The mechanical properties of the starch film with 41.8% glycerine in dependence on the limiting viscosity index [η]

| Sample No. | $T_B$ ° C. | $H_2O$ % | [η] ml/g | d mm | $\sigma_m$ MPa | $\epsilon_b$ % |
|---|---|---|---|---|---|---|
| 7 | 110 | 1.77 | 160.5 | 0.72 | 7.0 +/- 0.3 | 107 +/- 6 |
| 6 | 140 | 1.80 | 139.9 | 0.65 | 6.8 +/- 0.4 | 106 +/- 18 |
| 5 | 160 | 1.55 | 127.9 | 0.64 | 6.3 +/- 0.4 | 99 +/- 5 |
| 4 | 180 | 1.54 | 115.6 | 0.64 | 6.9 +/- 0.2 | 107 +/- 9 |
| 3 | 220 | 1.66 | 82.8 | 0.73 | 4.8 +/- 0.4 | 97 +/- 23 |
| 2 | 200 | 1.55 | 59.2 | 0.61 | 4.9 +/- 0.5 | 69 +/- 23 |
| 1 | 235 | 1.30 | 51.5 | 0.87 | 9.0 +/- 0.7 | 22 +/- 24 |

What is claimed is:

1. A mass comprising at least 45% by weight of an amorphous starch, water, and at least one organic softener in at least 12% by weight with respect to the weight of the water-free starch, wherein the mass is a homogenised mass having a limiting viscosity index of at least 40 ml/g, and wherein the starch has an amylopectin content of greater or equal 50% to by weight with respect to the weight of the starch in water-free condition and is obtainable from native or chemically-modified starch.

2. A mass according to claim 1, wherein the mass additionally contains a lubricant and releasing agent which is selected from the group consisting of lecithins, monoglycerides, diglycerides, and triglycerides, in particular glycerine monostearate, polyglycerine esters of nutient fatty acids, polyethylene esters of nutrient fatty acids, sugar esters of nutrient fatty acids and nutrient fatty acids.

3. A mass according to claim 1, wherein the softener is selected from the group consisting of polyalcohols, in particular glycerine, organic acids, hydroxy acids, amines, acid amides and sulphoxides, pyrrolidones.

4. A mass according to claim 2, wherein the mass contains glycerine monostearate and lecithin in a weight ratio of 1:1.5.

5. A mass according to claim 1, wherein the mass additionally contains an aggregate in a weight range of 3.5% by weight to 15% by weight with respect to the total weight of the mass, wherein the aggregate is selected from the group consisting of carbonates, hydrogen carbonates of alkali or earth alkali ions, amylases, further decomposing agents, colourings, preservatives, anti-oxidants, physically or chemically modified biopolymers and vegetable polypeptides.

6. A shape body, in particular a soft capsule casing, manufactured from a mass according to claim 1.

7. A shape body, in particular soft capsule casing, according to claim 6, wherein the shape body has an elongation at rupture of at least 100% at 25° C. and 60% relative humidity.

8. A shape body, in particular soft capsule casing according to claim 6, wherein the shape body at 25° C. and 60% relative air humidity has a strength, $\sigma_m$, of at least 2 MPa.

9. A shape body according to claim 6, wherein the shape body is a soft capsule and that the capsule casing comprises a thickness in the region between 0.1 and 0.2 mm.

10. A shape body, in particular soft capsule casing, according to claim 6, wherein the shape body consists of a multi-layered film and that at least two of the layers have a different chemical composition.

11. A starch-containing mass according to claim 1 wherein the limiting viscosity index of the homogenised mass is at least 50 ml/g.

12. A starch-containing mass according to claim 1 wherein the limiting viscosity index of the homogenised mass is at least 60 ml/g.

13. A mass according to claim 4, wherein the mass contains glycerine monostearate and lecithin in a weight ratio of 1:1.2.

14. A mass according to claim 4, wherein the mass contains glycerine monostearate and lecithin in a weight ratio of 1:1.

15. A mass according to claim 5, wherein the mass additionally contains an aggregate in a weight range of 5% by weight to 8% by weight.

16. A shape body, in particular soft capsule casing, according to claim 7, wherein the shape body has an elongation at rupture of at least 160% at 25° C. and 60% relative humidity.

17. A shape body, in particular soft capsule casing, according to claim 7, wherein the shape body has an elongation at rupture of at least 240% at 25° C. and 60% relative humidity.

18. A shape body, in particular soft capsule casing according to claim 8, wherein the shape body at 25° C. and 60% relative air humidity has a strength, $\sigma_m$, in the range of 3.5 MPa to 8 Mpa.

19. A shape body, in particular soft capsule casing according to claim 8, wherein the shape body at 25° C. and 60% relative air humidity has a strength, $\sigma_m$, in the range of 4 MPa to 6.5 Mpa.

20. A shape body according to claim 9, wherein the shape body is a soft capsule and that the capsule casing comprises a thickness in the region between 0.2 and 0.6 mm.

* * * * *